United States Patent [19]

Venturini

[11] Patent Number: 5,185,002
[45] Date of Patent: Feb. 9, 1993

[54] TRANSDUCER APPARATUS HAVING WATER HAMMER DAMPENING MEANS

[75] Inventor: Claudio Venturini, Corona Del Mar, Calif.

[73] Assignee: Alcon Surgical, Inc., Fort Worth, Tex.

[21] Appl. No.: 722,982

[22] Filed: Jun. 28, 1991

[51] Int. Cl.⁵ ............................................. A61B 17/20
[52] U.S. Cl. ........................................ 604/30; 73/707
[58] Field of Search ................. 604/22, 30; 137/599; 138/26; 73/707

[56] References Cited

U.S. PATENT DOCUMENTS

| | | | |
|---|---|---|---|
| 1,856,695 | 5/1932 | Florez | 73/707 |
| 1,941,613 | 1/1934 | McDonell | 138/26 |
| 1,958,009 | 5/1934 | McKee | 73/707 |
| 2,518,832 | 8/1950 | Stephens | 138/26 |
| 2,910,830 | 11/1959 | White | 138/26 |
| 2,932,200 | 4/1960 | Phillips | 73/707 |
| 3,323,305 | 6/1967 | Klees | 138/26 |
| 3,402,608 | 9/1968 | Nishigori | 73/707 |
| 3,589,363 | 6/1971 | Banko et al. | |
| 3,693,613 | 9/1972 | Kelman | |
| 3,902,495 | 9/1975 | Weiss et al. | |
| 3,915,008 | 10/1975 | Silverman et al. | 73/707 |
| 4,041,947 | 8/1977 | Weiss et al. | |
| 4,103,696 | 8/1978 | Cary | 138/26 |
| 4,496,342 | 1/1985 | Banko | 604/27 |
| 4,832,685 | 5/1989 | Haines | 604/30 |
| 4,921,477 | 5/1990 | Davis | 604/22 |
| 4,935,005 | 6/1990 | Haines | 604/30 |

FOREIGN PATENT DOCUMENTS

| | | | |
|---|---|---|---|
| 113836 | 10/1900 | Fed. Rep. of Germany | 138/26 |
| 555278 | 6/1923 | France | 73/707 |
| 1262181 | 10/1986 | U.S.S.R. | 138/26 |

OTHER PUBLICATIONS

General Fittings Co., "Shock Absorber" IEN-4300 Providence, R.I., Jul. 1938.

*Primary Examiner*—Stephen C. Pellegrino
*Assistant Examiner*—Ralph A. Lewis
*Attorney, Agent, or Firm*—Julie J. Cheng; Jeffrey S. Schira

[57] ABSTRACT

An improvement to a flow control system is disclosed which comprises a transducer apparatus having dampening means to prevent or reduce the destructive effect of water hammers in such fluid control systems. This is especially useful in surgical irrigation and aspiration systems. The dampening means functions by diverting the transient fluid waves away from the delicate pressure-sensing means until a portion of the kinetic energy contained therein is dispersed.

3 Claims, 2 Drawing Sheets

TRANSDUCER APPARATUS HAVING WATER HAMMER DAMPENING MEANS

BACKGROUND OF THE INVENTION

This invention relates to fluid flow control systems, such as surgical irrigation and aspiration systems, especially as used in ophthalmic surgery. In particular, this invention relates to the reduction or elimination of transient fluid waves at or near the pressure transducer apparatus in a surgical aspiration line. For purposes of this specification, the terms "fluid flow control," "fluid control" and "flow control" are used interchangeably.

Intraocular surgery, particularly cataract removal, has been greatly aided by the development of a procedure called phacoemulsification. The procedure involves the use of surgical instruments which include cutting or fragmenting means combined with means for irrigating the intraocular surgical site and aspirating therefrom the spent irrigating fluid, together with any tissue fragmented during the surgical procedure. See for example, U.S. Pat. No. 3,589,363 (Banko et al.). Improvements to that fluid control system are disclosed in U.S. Pat. Nos. 3,693,613 (Kelman); 3,902,495 (Weiss et al.); 4,041,947 (Weiss et al.); 4,496,342 (Banko); 4,832,685 (Haines); and 4,921,477 (Davis). The contents of each of the above-listed patents are hereby incorporated by reference in their entirety.

Phacoemulsification is accomplished by the use of an ultrasonic surgical tool capable of longitudinal vibrations such that, when the vibrating tool is applied to tissue (e.g., a cataractous lens), it is capable of fragmenting ocular tissue into small pieces. This tool is attached to a fluid system having means for supplying irrigation fluid to the surgical site and an aspiration means for removing the irrigation fluid and fragmented tissue from the surgical site. The aspiration means includes an axial bore through the ultrasonic tool which is connected to a source of fluid flow and vacuum, such as a pump, whereby the tissue fragments are evacuated form the surgical site along with the irrigation fluid.

Because the ultrasonic surgical tool fragments the excised tissue into tiny particles which are then removed from the surgical site along with the spent irrigation fluid, the incision in the eyeball need only be large enough to accommodate the tip of the tool therein and is therefore substantially smaller than the incision required to remove the lens in one piece. Thus, the surgical field is essentially a closed system and controlling the rate of fluid into and out of the eye becomes very important in order to prevent collapse of the anterior chamber of the eye. In particular, a blockage or occlusion may occur, for example, when a piece of fragmented tissue which is larger than the axial bore of the surgical tool is drawn against the entrance to the bore. When such a blockage occurs in the aspiration line, the negative pressure of the suction in the aspiration line between the surgical site and the pump increases. If the blockage is suddenly released, either by the mechanical action of the ultrasonic tool or by the increased value of the suction force, there is a tendency for the fluid within the surgical site to rush suddenly into the aspiration line, with possibly disastrous consequences. This is an especially important problem in ocular surgery because the total volume of the fluid in the surgical site is much smaller than the volume of fluid in the irrigation and aspiration lines.

Kelman (U.S. Pat. No. 3,693,613) was among the first to discuss the problems associated with maintaining a near-constant pressure within the fluid system. The system disclosed therein provides fluid control by the use of a relief valve located in the aspiration line upstream of the pump which opens the line to air when a change in the fluid pressure exceeds a pre-set level, as sensed by a transducer apparatus located in the aspiration line upstream of the relief valve. The Weiss et al. patents (U.S. Pat. No. 3,902,495 and U.S. Pat. No. 4,041,947) improve upon the flow control system of Kelman by limiting the flow rate of the irrigation fluid.

A second type of fluid flow control system is disclosed in Banko (U.S. Pat. No. 4,497,342). There, flow control is accomplished by the use of a second solution of infusion fluid (termed "surge fluid") which leads into the aspiration line. The valve which connects the surge fluid to the aspiration line is controlled by a transducer apparatus which is capable of sensing changes in the flow rate. In order to insure that the surge fluid, rather than the infusion fluid, is aspirated during a fluid surge, the surge fluid solution is placed at a higher level than the infusion fluid and therefore has a faster flow rate.

A third type of fluid flow control system, which improves upon the systems of both Kelman and Banko, is disclosed in Haines (U.S. Pat. No. 4,832,685). There, the fluid pressure is controlled by a line connecting the irrigation and aspiration lines. A valve located in the connecting line is normally closed, but is momentarily opened if there is an increased pressure in the aspiration line, as sensed by a pressure transducer apparatus located in the aspiration line. This fluid control system allows the excess vacuum in the aspiration line to be controllably and rapidly released after a partial or complete occlusion by venting to the irrigation line rather than to air. This liquid venting or pressure equalization system provides a faster rise time, reduces the chances of the occurrence of collapses of the enclosed surgical site (e.g. eye) and, further, requires only one irrigation bottle and the use of a check valve to prevent reversed irrigation flow towards the bottle when venting.

Davis (U.S. Pat. No. 4,921,477) improves upon the fluid flow control system of Haines by the inclusion of a dampening device. In Haines, due to the venting route, the non-compressible nature of liquids and the lack of air in the fluid system, the venting, or pressure equalization, causes an undesirable oscillating turbulence in the eye. The dampening device of Davis reduces or eliminates this undesirable oscillation. This dampening mechanism includes a membrane diaphragm along one side of a fluid chamber thereof which communicates directly with the aspiration line. The membrane absorbs the fluctuations caused by the displacement of fluid by the rollers of the peristaltic pump, thereby keeping the flow constant in the eye. A reflux shield of the dampening mechanism limits the outward movement of the diaphragm and a stop shield limits the inward movement of the diaphragm.

The fluid control systems of Haines and Davis utilize transducer apparatus to detect changes in pressure in the aspiration line, which, if the pressure change exceeds a pre-set limit, stops the pump and allows the surgeon to activate the venting mechanism. As used herein, the term "transducer apparatus" means the combination of one or more pressure-sensing means and the apparatus which connects said pressure-sensing means to the aspiration line. The transducer apparatus senses pressure changes in the aspiration line without impeding the flow of fluid and produces a corresponding electric signal which is transmitted to a control panel. If the change exceeds the pre-set limit, the control panel deactivates the and source, allowing the vacuum to remain relatively constant while the fluid flow stops. This permits the surgeon to activate the venting mechanism. The pre-set pressure level may be varied, according to a number of different factors, such as the mode or system function which a surgeon selects during the course of a surgical procedure.

When the fluid system is vented, fluid enters the aspiration line, often forming transient fluid waves (otherwise known as "water hammers") which enter the transducer apparatus and impact against the pressure-sensing means. Over time, or if a water hammer is of sufficient magnitude, these water hammers destroy the transducer apparatus, often also causing destruction of the surrounding circuitry.

There is therefore a need for a dampening device to prevent water hammers from destroying the transducer apparatus and surrounding circuitry in surgical irrigation and aspiration systems.

SUMMARY OF THE INVENTION

This invention is directed to a transducer apparatus for use in a surgical irrigation and aspiration system, wherein the transducer apparatus includes dampening means to prevent or reduce the destructive effect of water hammers on the delicate pressure-sensing means of the transducer apparatus. The dampening means acts as a "shock-absorber" by diverting the transient fluid wave away from the pressure-sensing means and allowing the residual air left in the transducer apparatus to compress and absorb a portion of the high levels of kinetic energy present in the transient fluid wave.

DETAILED DESCRIPTION OF THE INVENTION

Figure 1:
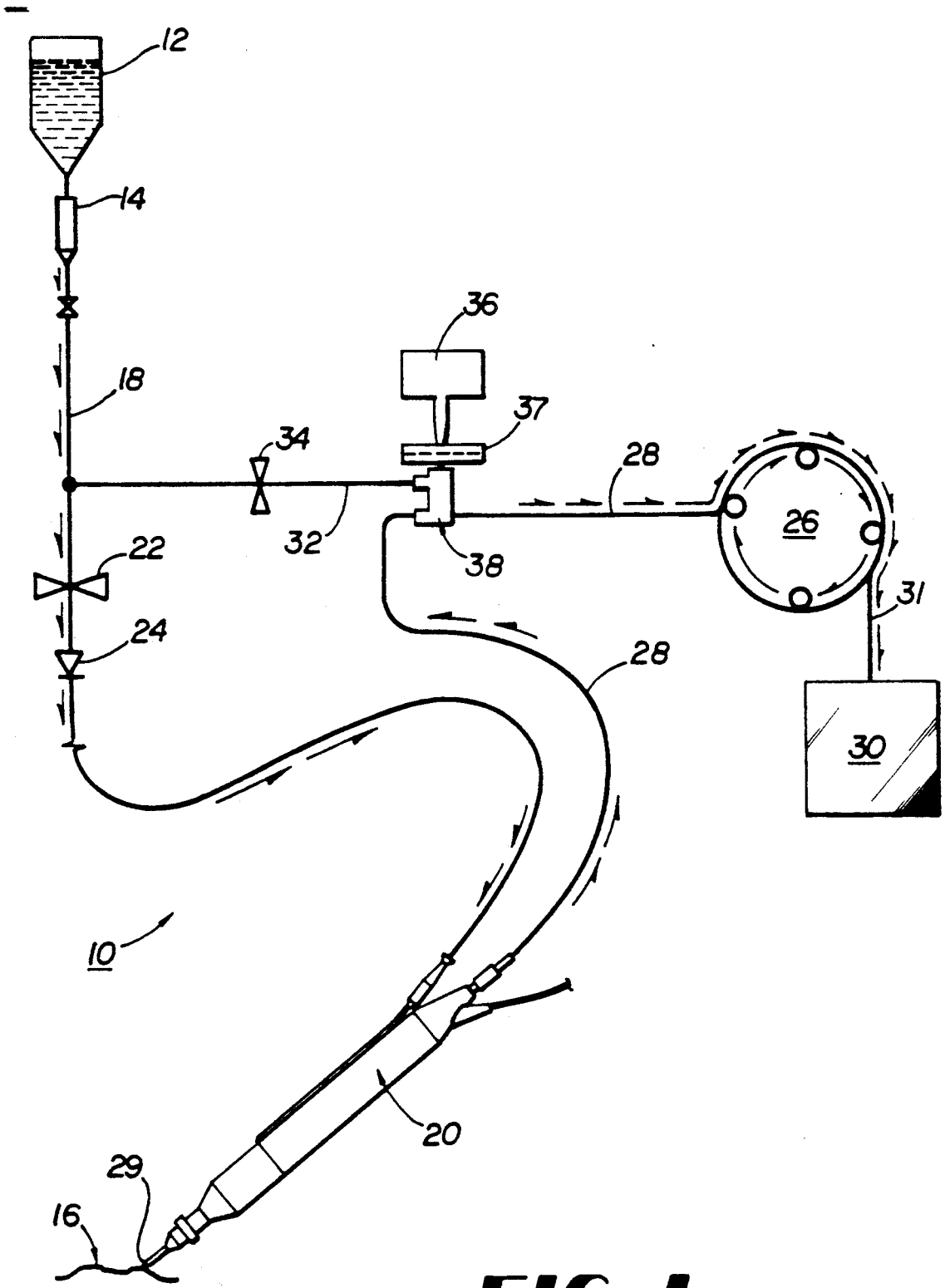
FIG. 1 is a schematic illustration of a representative fluid circuit of a surgical irrigation and aspiration system.

Referring to FIG. 1, a representative surgical irrigation and aspiration system of the present invention is illustrated schematically. The system 10 includes a bag or bottle 12 and a drip chamber 14 used to maintain a pressure in the eye 16 and to provide irrigation fluid. The bottle 12 is hung on a pole which, with the drip chamber 14, gives an even gravity flow or irrigation fluid through the irrigation line 18 to the handpiece 20 and then to the eye 16. A solenoid or valve 22 is positioned in the irrigation line 18 and is used to stop and start the irrigation fluid when needed and is operated by a footswitch controllable by the surgeon. A schematic or an electrical circuit including this footswitch which can be adapted and used to control this fluid flow control system is shown for example in U.S. Pat. No. 4,832,685. A one-way check valve 24 in the irrigation line 18 between the irrigation solenoid 22 and the handpiece 20 prevents the fluid from returning up or back flowing in the irrigation line 18 during venting, as will be described below.

A pump 26, or other vacuum source, provides a vacuum to evacuate spent irrigation fluid from the surgical site 16 through the handpiece 20, through the aspiration line 28 and then through drainage line 31 into a waste material drainage container or bag 30. When there is an occlusion in the aspiration line 28, such as at the tip 29 of the handpiece 20, a vacuum results in the aspiration line 28 as the pump 26 continues to exert a suction force thereto. This vacuum is relieved or vented by the influx of irrigation fluid along the pressure equalization or vent line 32 which directly communicates between the irrigation line 18 and the aspiration line 28. The vacuum is thereby quickly relieved by the head pressure of the bottle 12 via the vent solenoid or valve 34. This process is called "venting" the system.

The valve 34 is normally closed when the handpiece 20 is being used to aspirate fluid and tissue from a surgical site 16. When a blockage occurs in the aspiration line 28, such as when a tissue fragment occludes the axial bore in the ultrasonic tool of the handpiece 20, the increased suction in the aspiration line 28 is sensed by the pressure sensitive transducer apparatus 36, which in turn sends a signal to shut off the pump 26. The surgeon can then release the vacuum in the aspiration line 28 by momentarily opening the valve 34 to admit irrigation fluid from bottle 12 to the aspiration line 28 via the vent line 32 and through a special fitting 38 such as is shown and described in detail in U.S. Pat. No. 4,832,685. As soon as the pressure has been equalized, the transducer apparatus 36 detects the lower level of suction or vacuum and allows the surgeon to restart the pump 26. When the valve 34 is closed and the surgeon restarts the system, the pump 26 will again draw fluid from the aspiration line 28 and suction will thereby be reapplied to the surgical site. The check valve 24 prevents a backward surge of fluid in the irrigation line 18 when the valve 34 is open to permit irrigation fluid to flow into the aspiration line 28. A filter 37 is provided just upstream of the transducer apparatus 36 to prevent bacteria or ocular tissue from getting into the transducer apparatus.

In fluid control systems which vent to air rather than to fluid, such as described in the Kelman and Weiss patents, when a blockage occurs in the aspiration line and the increased suction is sensed by the pressure-sensitive transducer apparatus, the transducer signals the vent to flutter (to open and close rapidly), but the pump is not deactivated. The surgeon can then deactivate the pump and fully vent the system.

Figure 2:
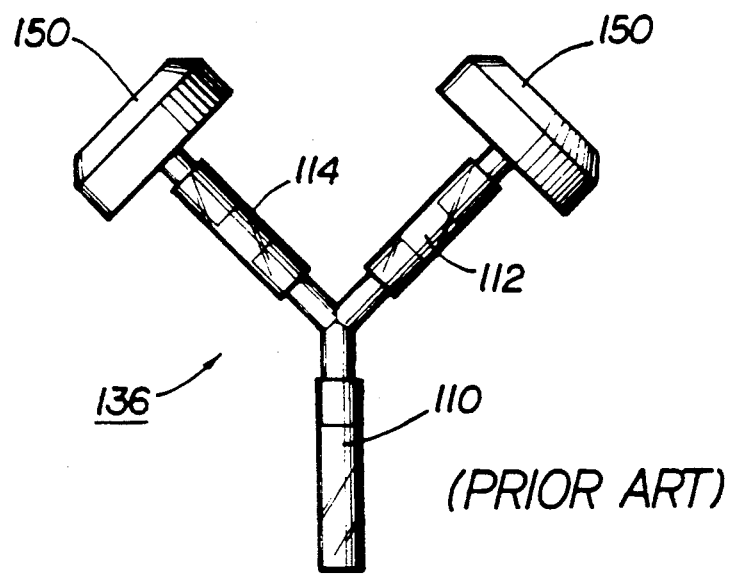
FIG. 2 illustrates a prior art transducer apparatus.

Referring now to FIG. 2, a prior art transducer apparatus 136 is illustrated. Fluid from the aspiration line 28 enters through fluid connector 110 and is divided between fluid lines 112 and 114, which each lead to pressure-sensing means 150. When the fluid system is operational, the fluid connector 110 and fluid lines 112 and 114 are filled with air and fluid, unlike the aspiration line, which is essentially filled with fluid only. This is because fluid lines 112 and 114 dead-end at pressure-sensing means 150; therefore, there is some residual air left in the transducer apparatus 136.

When the fluid system 10 vents, the irrigation fluid flowing through the vent line 32 and then through the aspiration line 28, creates a transient fluid wave. When the wave reaches the transducer apparatus 136, it impacts with full force on the delicate pressure-sensing means 150 (thus creating a "water hammer"). Due to the high level of kinetic energy present in such transient fluid waves, this repeated hammering on the transducer apparatus 136 usually results in the destruction of the pressure-sensing means 150, as well as the surrounding circuitry. In fact, one water hammer of sufficient magnitude may cause the destruction of the pressure-sensing means 150.

Figure 3:
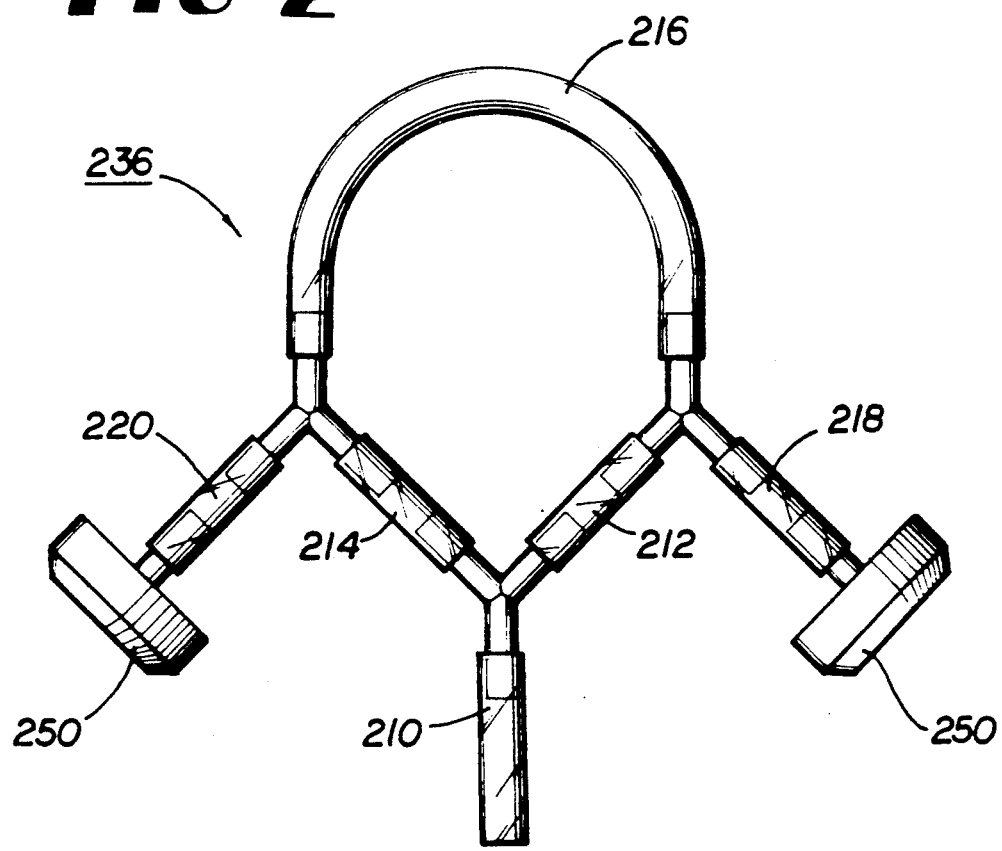
FIG. 3 illustrates the preferred embodiment of the transducer apparatus of the present invention.

Referring now to FIG. 3, the preferred embodiment of the invention is illustrated. The delicate pressure-sensing means 250 are now configured such that transient fluid waves will not impact with full force upon the pressure-sensing means 250; rather, the fluid enters fluid connector 210 and splits at the Y-junction to flow into fluid lines 212 and 214 which connect to dampening means 216, where the water hammer expends a portion of the kinetic energy contained therein by impacting against itself. Although fluid lines 212 and 214 also connect to fluid lines 218 and 220, which are in turn connected to the pressure-sensing means 250, the transient fluid waves coming from fluid lines 212 and 214 will flow into the dampening means 216 rather than into fluid lines 218 and 220, since fluid has a tendency to maintain a constant flow direction.

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A pressure sensing apparatus for use in combination with a surgical irrigation and aspiration system, comprising:
    a) at least a first pressure sensor and a second pressure sensor;
    b) a first fluid line in fluid communication with the first pressure sensor;
    c) a second fluid line in fluid communication with the second pressure sensor;
    d) a fluid connector in fluid communication with the first fluid line and the second fluid line; and
    e) a means for diverting transient fluid pressure away from the first pressure sensor and the second pressure sensor connected between the first fluid line and the second fluid line and in fluid communication with the fluid connector through the first fluid line and the second fluid line.

2. The pressure sensing apparatus of claim 1 wherein the means for diverting transient fluid pressure away from the first pressure sensor and the second pressure sensor comprises a fluid conduit.

3. A pressure sensing apparatus for use in combination with a surgical irrigation and aspiration system, comprising:
    a) at least a first pressure sensor and a second pressure sensor;
    b) a first fluid line in fluid communication with the first pressure sensor;
    c) a second fluid line in fluid communication with the second pressure sensor;
    d) a fluid connector in fluid communication with the first fluid line and the second fluid line; and
    e) a fluid conduit connected between the first fluid line and the second fluid line for diverting transient fluid pressure away from the first pressure sensor and the second pressure sensor in fluid communication with the fluid connector through the first fluid line and the second fluid line.

* * * * *